US011851386B2

(12) United States Patent
Mukherjee et al.

(10) Patent No.: US 11,851,386 B2
(45) Date of Patent: Dec. 26, 2023

(54) SOLID-ACID CATALYZED PARAFFIN ALKYLATION WITH RARE EARTH-MODIFIED MOLECULAR SIEVE ADSORBENTS

(71) Applicant: Exelus Inc., Fairfield, NJ (US)

(72) Inventors: Mitrajit Mukherjee, Livingston, NJ (US); Vamsi M. Vadhri, Edison, NJ (US); Zawer Wojokh, Little Falls, NJ (US); Narendra Joshi, Jersey City, NJ (US)

(73) Assignee: EXELUS, INC., Fairfield, NJ (US)

( * ) Notice: Subject to any disclaimer, the term of this patent is extended or adjusted under 35 U.S.C. 154(b) by 0 days.

(21) Appl. No.: 17/966,697

(22) Filed: Oct. 14, 2022

(65) Prior Publication Data

US 2023/0119464 A1 Apr. 20, 2023

Related U.S. Application Data

(60) Provisional application No. 63/256,516, filed on Oct. 15, 2021.

(51) Int. Cl.
*C07C 2/62* (2006.01)
*B01J 29/08* (2006.01)
*B01J 29/14* (2006.01)
*B01J 37/30* (2006.01)
*B01J 37/08* (2006.01)
*B01J 29/12* (2006.01)
*B01J 29/00* (2006.01)

(52) U.S. Cl.
CPC .............. *C07C 2/62* (2013.01); *B01J 29/005* (2013.01); *B01J 29/082* (2013.01); *B01J 29/085* (2013.01); *B01J 29/087* (2013.01); *B01J 29/12* (2013.01); *B01J 29/123* (2013.01); *B01J 29/126* (2013.01); *B01J 29/14* (2013.01); *B01J 29/143* (2013.01); *B01J 29/146* (2013.01); *B01J 37/088* (2013.01); *B01J 37/30* (2013.01); *B01J 2229/183* (2013.01); *B01J 2229/37* (2013.01); *C07C 2523/10* (2013.01); *C07C 2523/42* (2013.01); *C07C 2523/44* (2013.01); *C07C 2529/89* (2013.01)

(58) Field of Classification Search
CPC ......... C07C 2/62; C07C 2/58; C07C 2523/10; C07C 2523/42; C07C 2523/44; C07C 2529/00; C07C 2529/08; C07C 2529/12; C07C 2529/89; B01J 38/10; B01J 37/088; B01J 37/30; B01J 29/005; B01J 29/082; B01J 29/085; B01J 29/087; B01J 29/088; B01J 29/12; B01J 29/123; B01J 29/126; B01J 29/14; B01J 29/143; B01J 29/146; B01J 29/80; B01J 2229/183; B01J 2229/186; B01J 2229/42; B01J 2229/37
USPC ...... 585/713, 716, 721, 722; 502/64, 65, 66, 502/67, 69
See application file for complete search history.

(56) References Cited

U.S. PATENT DOCUMENTS

| | | |
|---|---|---|
| 3,851,004 A | 11/1974 | Yang |
| 3,893,942 A | 7/1975 | Yang |
| 3,917,738 A | 11/1975 | Fenske |
| 3,962,133 A | 6/1976 | Rodewald |
| 4,116,880 A | 9/1978 | Olah |
| 4,384,161 A | 5/1983 | Huang |
| 5,012,033 A | 4/1991 | Child et al. |
| 5,120,897 A | 6/1992 | Del Rossi et al. |
| 5,157,196 A | 10/1992 | Crossland et al. |
| 5,157,197 A | 10/1992 | Cooper et al. |
| 5,190,904 A | 3/1993 | Crossland et al. |
| 5,220,095 A | 6/1993 | Hommeltoft et al. |
| 5,221,777 A | 6/1993 | Huss, Jr. et al. |
| 5,245,101 A | 9/1993 | Del Rossi et al. |
| 5,288,685 A | 2/1994 | Kallenbach et al. |
| 5,324,881 A | 6/1994 | Kresge |
| 5,346,676 A | 9/1994 | Crossland et al. |
| 5,364,976 A | 11/1994 | Kallenbach |
| 5,391,527 A | 2/1995 | Kojima et al. |
| 5,475,178 A | 12/1995 | Del Rossi et al. |
| 5,489,729 A | 2/1996 | Benazzi et al. |
| 5,731,256 A | 3/1998 | Benazzi et al. |
| 5,739,074 A | 4/1998 | Kocal et al. |
| 5,986,158 A | 11/1999 | Van Broekhoven et al. |
| 7,459,412 B2 | 12/2008 | Lercher et al. |
| 9,656,255 B2 * | 5/2017 | Long ................. B01J 29/80 |
| 11,261,139 B2 * | 3/2022 | Mukherjee ........... B01J 29/082 |

FOREIGN PATENT DOCUMENTS

| | | |
|---|---|---|
| GB | 1389237 A | 4/1975 |
| GB | 1432720 A | 4/1976 |
| JP | H01245853 A | 10/1989 |
| WO | 1995026815 A1 | 10/1995 |

OTHER PUBLICATIONS

Lutz, W., Rüscher, C. H., Gesing, T. M., Stöcker, M., Vasenkov, S., Freude, D., . . . Berger, C. "Investigations of the mechanism of dealumination of zeolite y by steam: Tuned mesopore formation versus the Si/Al ratio. Studies in Surface Science and Catalysis", (2004) vol. 154, 1411-1417.

(Continued)

*Primary Examiner* — Elizabeth D Wood
(74) *Attorney, Agent, or Firm* — Frank Rosenberg

(57) ABSTRACT

This invention describes methods of alkylating isobutane which include a catalytic reaction system comprising a crystalline zeolite catalyst and a rare earth-modified molecular sieve adsorbent (RE-MSA). The crystalline zeolite catalyst comprises sodalite cages and supercages, a Si/Al molar ratio of 20 or less, less than 0.5 weight percent alkali metals; and up to 5 wt % of Pt, Pd and or Ni, and acid-site density (including both Lewis and Brønsted acid sites) of at least 100 mole/gm. The RE-modified molecular sieve adsorbent (Re-MSA) comprising sodalite cages and supercages, a Si/Al molar ratio of 20 or less, less than 1 wt % of alkali metals, RE (rare earth elements) in the range of 10 to 30 wt % and transition metals selected from groups 9-11 in the range from 2 wt % to 10 wt; and acid-site density of no more than 30 mole/gm. The invention also includes methods of making RE-MSA.

20 Claims, 1 Drawing Sheet

(56) References Cited

OTHER PUBLICATIONS

Herden, H. et al. "Liquid phase adsorption studies of octene-1 and octane on X-zeolites." Journal of Colloid and Interface Science 102 (1984): 227-231.

Ho, W. S.; Doyle, G.; Savage, D. W.; Pruett, R. L. "Olefin separations via complexation with cuprous diketonate", Ind. Eng. Chem. Res. 1998, 27, 334.

Safarik, D. J., & Eldridge, R. B. "Olefin/Paraffin Separations by Reactive Absorption: A Review", Industrial & Engineering Chemistry Research, 37(7) (1998) 2571-2581.

Liu, Y.; Li, R.; Sun, H.; Hu, R. "Effects of catalyst composition on the ionic liquid catalyzed isobutane/2-butene alkylation", J. Mol. Catal. A: Chem. 2015, 398, 133-139.

Padin, J.; Yang, R. T.; Munson, C. L. "New Sorbents for Olefin/Paraffin Separations and Olefin Purification for C4 Hydrocarbons", Ind. Eng. Chem. Res. 1999, 38, 3614-3621.

Takahashi, A. et al. "Influence of Ag Content and H2S Exposure on 1,3-Butadiene/ 1-Butene Adsorption by Ag Ion-Exchanged Y-Zeolites (Ag—Y)", Ind. Eng. Chem. Res. 2001, 40, 3979-3988.

Takahashi, A.; Yang, R. T. et al. "Cu(I)—Y Zeolite as a Superior Adsorbent for Diene/Olefin Separation", Langmuir 2001, 17, 8405-8413.

Jin, M.; Kim, S. S.; Kim, Y. D.; Park, J.-N.; Kim, J. H.; Ko, C. H.; Kim, J.-N.; Kim, J. M. "Redox-buffer effect of Fe2+ ions on the selective olefin/paraffin separation and hydrogen tolerance of a Cu+-based mesoporous adsorbent", J. Mater. Chem. A 2013, 1, 6653-6657.

Yang, R. T., & Kikkinides, E. S. "New sorbents for olefin/paraffin separations by adsorption via π-complexation", AIChE Journal (1995) 41(3), 509-517.

Wu, Z.; Han, S. S.; Cho, S. H.; Kim, J. N.; Chue, K. T.; Yang, R.T. "Modification of Resin-Type Adsorbents for Ethane/Ethylene Separation", Ind. Eng. Chem. Res. 1997, 36 ( 7) 2749-2756.

Padin, J.; Yang, R. T. "Tailoring New Adsorbents Based on π-Complexation: Cation and Substrate Effects on Selective Acetylene Adsorption", Ind. Eng. Chem. Res. 1997, 36, 4224-4230.

Rege, S. U., Padin, J., & Yang, R. T. "Olefin/paraffin separations by adsorption: π-Complexation vs. kinetic separation", AIChE Journal, 44(4) (1998) 799-809.

Padin, J., & Yang, R. T. "New sorbents for olefin/paraffin separations by adsorption via π-complexation: synthesis and effects of substrates", Chemical Engineering Science 55(14) (2000) 2607-2616.

Denayer, Joeri & Huybrechts, Bart & Depla, Anouschka & Hermans, Yves & Gemoets, Frederik & Buren, Frederik & Kirschhock, Christine & Baron, Gino & Pierre, Jacobs. "Removal of cyclopentadiene from 1-octene by transition metal containing zeolites. Part 1: Screening of the adsorption properties", Microporous and Mesoporous Materials 103 (2007) 1-10.

Denayer, Joeri & Depla, Anouschka & Vermandel, Walter & Gemoets, Frederik & Buren, Frederik & Martens, Johan & Kirschhock, Christine & Baron, Gino & Pierre, Jacobs. "Removal of cyclopentadiene from 1-octene by transition metal containing zeolites—Part 2: Stabilization of CoCaX zeolite by its cation distribution", Microporous and Mesoporous Materials. 103 (2007) 11-19.

Jayaraman, A., Yang, R. T., Munson, C. L., & Chinn, D. Deactivation of π-Complexation Adsorbents by Hydrogen and Rejuvenation by Oxidation. Industrial & Engineering Chemistry Research, 40(20) (2001) 4370-4376.

Machine Translation of JP H01245853 A.

* cited by examiner

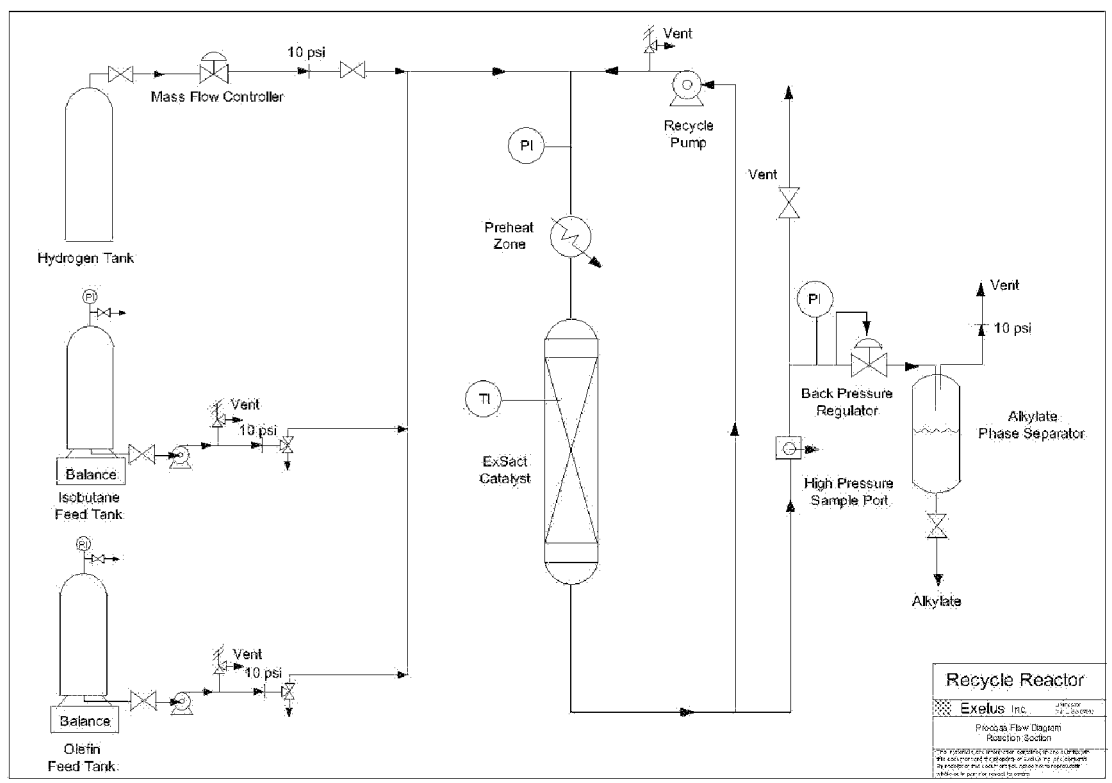

SOLID-ACID CATALYZED PARAFFIN ALKYLATION WITH RARE EARTH-MODIFIED MOLECULAR SIEVE ADSORBENTS

RELATED APPLICATIONS

This application claims the priority benefit of U.S. Provisional Patent Application Ser. No. 63/256,516 filed Oct. 15, 2021.

BACKGROUND

High-octane alkylate is the cleanest gasoline blending stream produced in a refinery. The term "alkylate" refers to the reaction product of isobutane with olefins. Alkylate is an ideal clean fuel component because pollution from alkylate is low and alkylate has low toxicity. Alkylate has been blended into gasoline for decades to improve octane and thus the antiknock properties of gasoline. Alkylate's importance to refiners continues to grow. It makes up about 13%, or more than 12 million barrels per day, of current North American fuel. For the refiner striving to meet the stricter motor fuel specifications being mandated on an expanding worldwide basis, investment in alkylation capacity can lead to enhanced refinery flexibility and profitability. Alkylate is made currently using liquid acid catalysts. Refiners typically use either hydrofluoric acid (HF), which can be deadly if spilled, or sulfuric acid ($H_2SO_4$), which also potentially is harmful and increasingly costly to recycle.

In an alkylation reaction, light olefins are reacted with iso-paraffins (typically iso-butane) in the presence of a strong acid catalyst. The alkylation of isobutane with $C_2$-$C_5$ olefins involves a series of consecutive and simultaneous reactions occurring through carbocation intermediates. The first step is the addition of a proton to the isobutane to form a tert-butyl, or t-butyl cation. The t-butyl cation then is added to an olefin to give the corresponding $C_8$ carbocation. These $C_8$ carbocations may isomerize via hydride transfer and methyl shifts to form more stable cations. Then the $C_8$ cations undergo rapid hydride transfer with isobutane, to form the desired iso-octane molecule, and the t-butyl cation is regenerated to perpetuate the chain sequence.

Unfortunately, these are not the only reactions occurring during alkylation. There are a number of secondary reactions that, in general, tend to reduce the quality of the alkylate. Polymerization results from the addition of a second olefin to the $C_8$+ cation formed in the primary reaction, thereby forming cations with more than 8 carbon atoms, such as $C_{12}$+ cations. The $C_{12}$+ cation can continue to react with an olefin to form a larger cation. The successive addition of olefins to carbocations, or olefin polymerization, is believed generally to be the primary route to catalyst deactivation. The olefin addition reaction sometimes is referred to as a polymerization step, while the hydride-transfer reaction is denoted as the main alkylation reaction. The polymerization reaction results in the formation of "coke". The heavier alkylate molecules can then crack over the acid sites to form lighter $C_5$-$C_7$ hydrocarbons. As a result, alkylate consists of paraffinic molecules from light iso-pentane ($C_6H_{12}$) to heavier ($C_{12}H_{26}$ and larger) hydrocarbons.

Solid acid catalysts have been investigated as alternatives to liquid catalysts for nearly 30 years. Some of these catalysts include $AlCl_3$; platinum compounds; heteropolyacids, such as tungstates; and liquid acids immobilized on silica, polymers, or other solid supports. Natural or artificial zeolites also have been used. Solid acid catalysts can be tuned to improve selectivity and reduce production costs, but they tend to deactivate rapidly under alkylation reaction conditions through two mechanisms: 1) "Coke" formation on active sites from olefin polymerization reaction and 2) Pore-mouth plugging by heavy alkylate molecules The heavy hydrocarbons tend to plug the pore structure of solid catalysts, thereby reducing access to acidic sites.

There has been great interest in developing improved solid acid alkylation catalysts. For example, Japanese Patent Application No. 1-245853, U.S. Pat. Nos. 3,962,133 and 4,116,880, and United Kingdom Patent Nos. 1,432,720 and 1,389,237, disclose $H_2SO_4$ enhanced super acid catalysts; U.S. Pat. Nos. 5,220,095, 5,731,256, 5,489,729, 5,364,976, 5,288,685 and European Patent Application No. 714,871A, disclose $CF_3SO_3$ H/silica catalysts; U.S. Pat. Nos. 5,391,527, and 5,739,074, disclose Pt—$AlCl_3$—KCl/$Al_2O_3$catalysts; U.S. Pat. Nos. 5,157,196, 5,190,904, 5,346,676, 5,221,777, 5,120,897, 5,245,101, 5,012,033, 5,157,197, and published PCT Application No. WO 95/126,815, etc. disclose Lewis acid catalysts, such as $SbF_5$, $BF_3$ and $AlCl_3$; U.S. Pat. Nos. 5,324,881, and 5,475,178, disclose supported heteropolyacid catalysts; U.S. Pat. Nos. 3,917,738 and 4,384,161, disclose molecular sieve catalysts. Nonetheless, despite continued efforts over 50 years, there is still an unmet need for an improved, stable and economical solid acid alkylation catalyst.

Solid acid catalysts, such as zeolite catalysts that have a plurality of $H^+$, or acid sites, which are less toxic and less dangerous; however, such catalysts have fewer $H^+$, or acid sites than liquid acid catalysts, and only a portion of such acid sites are strong enough to catalyze alkylation reactions. Fundamentally different from liquid acids, zeolites have different populations of sites which differ substantially in their nature (Brønsted vs Lewis acids) and strength. Depending on the type of zeolite, its aluminum content, and the exchange procedure, Brønsted and Lewis acid sites having a wide range of strength and concentration are present. Zeolites exhibit a considerably lower proton (acid site) concentration than liquid acids. For example, 1 g of $H_2SO_4$ contains $20\times10^{-3}$ moles of protons, whereas 1 g of zeolite HY, with a Si/Al ratio of five, contain no more than $1\times10^{-3}$ moles of protons out of which 20-30% are strong enough to catalyze the alkylation reaction. As a result, the useful lifetime of a solid-acid catalyst is usually 2 orders of magnitude shorter than a liquid acid catalyst making it difficult to develop commercially viable paraffin alkylation technologies using solid-acid catalysts.

Methods of making zeolite catalysts having improved characteristics for alkylation have been described by Lercher et al. in U.S. Pat. No. 7,459,412. The catalysts described in this patent contain a crystalline zeolite with a silica ($SiO_2$) to Alumina ($Al_2O_3$) molar ratio less than 10, and an alkali metal content of 0.2 wt % or less. In the examples, Lercher et al. treated a commercial zeolite X with lanthanum nitrate, and then ammonium nitrate, and calcined at 450° C. in flowing air to result in the low alkali metal content zeolite catalyst. Lercher et al. reported that the catalyst should have the highest possible concentration of Brønsted acid centers and a low concentration of strong Lewis acid centers. The Lewis acid centers are catalytically inactive, but bind olefins that accelerate oligomerization and deactivation of the catalyst. Lercher et al. report that the Lewis acid centers arise from aluminum cations that are released from the crystal lattice during the calcination step.

Prior art methods that do not combine the rare earth treatments with deammoniation have described deammoniation temperatures of at least 500° C. See U.S. Pat. Nos. 3,893,942, 3,851,004, and 5,986,158.

The release of aluminum from the zeolite crystal lattice is known as dealumination and occurs at elevated temperature in the presence water vapor. For example, Lutz et al. in "Investigations of the Mechanism of Dealumination of Zeolite Y by Steam: Tuned Mesopore Formation Versus the Si/Al Ratio," in the Proceedings of the 14$^{th}$ Int'l Zeolite Conf., pp. 25-30 (2004) reported on the dealumination of zeolite Y at 1 bar water vapor at 500° C., 600° C., and 700° C. showing increasing rates of dealumination with increasing temperature.

INTRODUCTION

It is well known in literature that molecular sieve sorbents can be employed to separate olefins from paraffins. The adsorbents employed in the separation processes are generally crystalline aluminosilicates modified with a metal. Specifically, NaX zeolites can be used as an adsorbent in the separation field due to their stronger framework polarity which in turn can generate a stronger interaction with polar groups. Herden et al. studied the liquid phase adsorption of 1-octene and octane on ion-exchanged X zeolites[1]. They showed that the heats of immersions were higher for 1-octene than octane presumably due to the specific interaction of 1-octene with the cations. Their results also showed a strong influence of the nature of cations in the zeolites. For instance, they showed that the self-diffusivities of 1-octene decreased in the sequence KX>NaX>BaX. However, adsorbents like zeolites exchanged with alkali and alkaline earths, which mainly display Van der Waals interactions between framework and sorbate, are not sufficiently selective for the complete removal of less polar contaminants. Separation via more specific interactions between adsorbent and adsorbate is often necessary. In many cases, metals are ion-exchanged onto the zeolite which generally results in an increase in capacity of the sieves for the adsorption of unsaturated compounds. The d-orbitals of these metals can participate in bond-formation with unsaturated hydrocarbons in a nonclassical manner. This type of bonding is broadly referred to as π-complexation[2,3]. Many metals, especially transition metals such as Cu, Ag, Co, Ni etc. have been investigated for this purpose. π-complexation has been successfully applied for olefin/paraffin separation using liquid solutions containing silver or cuprous ions.[4-6] The selective adsorption of olefins over paraffins in the liquid phase has been used successfully for various applications. For instance, Liu et al.[7] found that mixtures of CuCl and chloroaluminate ionic liquids catalyze the isobutane/butene alkylation reaction more efficiently than pure chloroaluminate ionic liquids because the resulting CuAlC14 can reversibly adsorb part of butene and hence increase the isobutane/butene ratio in the reaction consequently reducing side reactions and improving the selectivity of TMP.

There have been a number of attempts to use 7C-complexation to separate olefin/paraffin mixtures in gas-solid systems too. Padin et al.[8] showed that monolayer-dispersed $AgNO_3/SiO_2$ displayed high selectivity and capacity for 1-butene over 1-butane thus acting like an excellent separating sorbent. Purification of 1-butene by removing trace amounts of 1,3-butadiene was achieved by using Ag+-exchanged Y-zeolite. The effect of varying silver content in Ag—Y on 1,3-butadiene adsorption was systematically studied using Ag—Y with different Si/Al ratios and Ag+-Na+ mixed ion-exchanged zeolites (AgNa—Y).[9] It was reported that AgNa—Y with an Ag content of 26 wt % Ag exhibited superior purification characteristics for this application. On the other hand, Takahashi et al.[10] reported that the conversion of Cu2+ to Cu+ in ion-exchanged zeolite Y, produced a new adsorbent for the separation of 1-butene/1,3-butadiene. They reported that the performance Cu(I)-Y was found to be superior to that of Ag—Y by approximately an order of magnitude. Additionally, Cu—Y also exhibited superior poisoning resistance to Ag—Y with respect to exposure to H2S/H2. Jin et al.[11] developed a novel mesoporous adsorbent, Fe—Cu/MCM-41, for the selective separation of of 1-butene/n-butane. The authors reported that co-impregnation of Fe2+ ions with Cu+ ions within the mesopores of MCM-41 gives superior 1-butene/n-butane separation ability compared to that of Cu-MCM-41 presumably because the $Fe^{2+}$ species acted as a kind of redox buffer and improved the chemical stability of Cu+ species which are responsible for π-complexation with olefins. Other sorbents based on π-complexation were also reported in literature for selective olefin adsorption: Ag+—exchanged resins,[12,13] monolayer CuCl on pillared clays,[14] and monolayer $AgNO_3/SiO_2$.[15-17]

Denayer et al.[18,19] evaluated a series of (transition) metal exchanged zeolites with different topology and Si/Al ratio for their potential to remove cyclopentadiene (CPD) from 1-octene. Co, Ni and Ag exchanged high-alumina zeolites were chosen as candidates for site-specific interaction. The authors reported that among all tested materials, zeolite X first exchanged with calcium ions, then calcined and subsequently exchanged with cobalt ions (denoted as CoCaX50) shows the highest adsorption selectivity and capacity.

The effects of $H_2$ and $H_2S$ exposure on 1,3-butadiene/1-butene adsorption by Ag—Y were examined in literature[9,20]. Based on XPS analysis, it is believed that Ag+ in Ag—Y reacted with $H_2S$ to form Ag2S causing a reduction of adsorption capacity. However, the separation factors for 1,3-butadiene/1-butene were still high enough for the purification application to be viable. On the other hand, $H_2$ exposure to Ag—Y was detrimental owing to the reduction of Ag+ to Ag0 resulting in a significant deterioration of π-complexation. Regeneration by oxidation was proposed as a solution which was successfully demonstrated and an optimum oxidation condition with respect to olefin adsorption was identified.

SUMMARY OF THE INVENTION

In a first aspect, the invention provides a method of alkylating isobutane, comprising: passing a feed mixture consisting of excess isobutane and C2 to C5 olefins into a reaction chamber; wherein the reaction chamber comprises: a crystalline zeolite catalyst comprising sodalite cages and supercages, a Si/Al molar ratio of 20 or less, less than 0.5 weight percent alkali metals; and up to 5 wt % of Pt, Pd and or Ni, and acid-site density (including both Lewis and Brønsted acid sites) of at least 100 μmole/gm; a Rare-Earth (RE)-modified molecular sieve adsorbent (MSA) comprising sodalite cages and supercages, a Si/Al molar ratio of 20 or less, less than 1 wt % of alkali metals, RE (rare earth elements) in the range of 10 to 30 wt % and transition metals selected from groups 9-11 in the range from 2 wt % to 10 wt; and acid-site density of no more than 30 μmole/gm. Note that these values refer to the zeolites and not to binders, fillers, or other structural components. Acid site density is measurable by conventional means such as defined in ASTM D4824-94 (reapproved 1998). Preferably, the catalyst and adsorbent are in the form of pellets or beads.

The invention likewise includes a catalytic reaction system comprising the catalyst and adsorbent as defined above. The system can be further characterized by features of apparatus and reaction conditions.

The invention can be further characterized by one or any combination of the following features: wherein, at steady state, at least 90% of the C2-C5 olefins are converted to products and wherein the Research Octane Number (RON) remains above 90; and conducting the process for a catalyst age of 2.5 or greater over the same catalyst without regeneration; and wherein steady state means that the selectivity to C8 isomers changes by 10% or less over the entire period that the catalyst age is determined; wherein the crystalline zeolite catalyst comprises rare earth elements in the range of 10 to 35 wt %; wherein the Re-MSA comprises a micro-pore diameter of at least 8 Angstroms, or in the range of 8 to 12 Å; the method conducted at a pressure of 250 to 400 psig; wherein the concentration of C2 to C5 olefins in the feed is between 1 wt % and 30 wt %; wherein the ratio of the concentration of iso-butane to the concentration of C2-C5 olefins at the entrance of the catalyst bed is between 100-1000 mol/mol; wherein the olefin space velocity is between 0.05/hr to 0.5/hr; wherein the catalyst and/or Re-MSA is regenerated in a flowing gas stream that is essentially hydrogen at a temperature of at least 250° C.; wherein the catalyst comprises 0.1 wt % to 5 wt %, or 0.5 to 4 wt %, or 1.0 to 3.0 wt %, of an element selected from the group consisting of Pt, Pd, Ni, and combinations thereof; wherein the catalyst and Re-MSA is regenerated with a flow of gas which is at least 50 volume % hydrogen; wherein the catalyst and Re-MSA is regenerated in flowing hydrogen at a temperature of at least 250° C. and a GHSV of at least 500; wherein the method is run continuously for a catalyst age of 2-3.5 without regenerating the catalyst or Re-MSA; wherein the reaction chamber comprises a packed catalyst bed followed by a Re-MSA bed; wherein the reaction chamber comprises a packed Re-MSA bed followed by a catalyst bed; wherein the reaction chamber comprises alternating beds of catalyst and Re-MSA comprising at least 2 catalyst beds and 2 Re-MSA beds; wherein the reaction chamber comprises a packed bed consisting of mixture of catalyst and Re-MSA; wherein the ratio of the Re-MSA weight to catalyst weight in the reaction chamber is between 0.1 to 10 wt/wt; wherein the reaction chamber comprises a packed bed of particles, comprising catalyst and Re-MSA wherein at least 95 wt % of the particles have particle diameters of at least 0.1 mm; the method conducted at a temperature between 45 and 90° C.; wherein the C2 to C5 olefin contains less than 100 ppm water; comprising conducting the process for a catalyst age of at least 2.5 or a catalyst age of at least 3.0 or a range of 2.5 to 5.0 or 4.0; and/or wherein the MSA is 13X molecular sieve.

In another aspect, the invention provides a method of making RE-modified molecular sieve adsorbent (Re-MSA), comprising: providing a molecular sieve adsorbent (MSA) comprising sodalite cages and super-cages and having a Si/Al molar ratio of 20 or less, and a first concentration of alkali metal; contacting the MSA with a solution comprising a rare earth metal; calcining said catalyst by heating said Re-MSA to a temperature of at least 575° C. to produce a Re-MSA intermediate comprising the rare earth metal and second concentration of alkali metal that is less than the first concentration of alkali metal; contacting the RE-MSA intermediate with a solution of a transition metal salt selected groups 9-11, drying to remove excess solution, and heating to a temperature to convert the transition metals salts to their oxide form.

The invention can be further characterized by one or any combination of the following features: wherein the step of calcining to a temperature of at least 575° C., preferably 600° C., thereby provides a RE-MSA in which a portion of the alkali metal cation sites are replaced with rare earth metal cation sites; wherein the step of contacting with a solution of transition metal salts, thereby provides a catalyst in which a portion of the alkali metal cation sites are replaced with rare earth metal cation sites, and another portion of the alkali metal cation sites are replaced with transition metals cation sites; and further wherein the heating to a temperature step does not exceed 450° C., and occurs in the presence of air; wherein the rare earth metal is selected from the group consisting of lanthanum, cerium, neodymium, and praseodymium, and said rare earth metal cations are selected from the group consisting of lanthanum cations, cerium cations, neodymium cations, and praseodymium cations; wherein the rare earth metal comprises lanthanum; wherein the alkali metal cation sites comprise at least 90 wt % sodium cation sites; wherein the catalyst has a silica to alumina ratio of from about 2 to about 35; wherein the catalyst has a silica to alumina ratio of from about 2 to about 10; wherein the solution comprising a rare earth metal comprises an aqueous $La(NO)_3$ solution; wherein the solution comprising a rare earth metal comprises an aqueous $La2(SO4)3$ solution; wherein the solution comprising a rare earth metal comprises an aqueous $LaCl3$ solution; wherein the solution comprising a rare earth metal comprises an aqueous solution of at least 0.1 M Lanthanum ions or at least 0.2 M La, or at least 0.4 M La, or at least 0.6 M La, or at least 0.8 M La, or in the range of 0.2 to 0.8 M La; wherein the catalyst is contacted with the rare earth metal solution at a temperature of from 60 to 90° C.; wherein the catalyst is contacted with the rare earth metal solution for a period of time of about 2 hours; wherein the step of calcining does not exceed 600° C.; wherein the step of calcining is conducted from 2 to 8 hours; wherein, during the calcination step, the Re-MSA is heated in the presence of air which has a moisture content that does not exceed 2.0 wt. % or does not exceed 0.2 wt; wherein the solution of transition metal salts comprises an aqueous solution of at least 0.1 M, or at least 0.2 M, or at least 0.3 M, or at least 0.5 M, or at least 1 M metal ions; wherein the step of contacting solution of transition metal salts, which provides a RE-MS A in which a portion of the alkali metal cation sites are replaced with transition metal cation sites, comprises an aqueous solution of nitrate, chloride, sulfate, acetate, citrate or oxolate salts; and/or wherein the MSA is 13X.

BRIEF DESCRIPTION OF THE DRAWING

FIG. 1 schematically illustrates the test unit used for screening adsorbents.

GLOSSARY

Catalyst Age—"Catalyst age" is the mass of olefin fed to the reactor divided by the mass of catalyst+ mass of adsorbent.

Catalyst Lifetime—The catalyst age at which the olefin conversion falls below 90% is defined as the "catalyst lifetime."

Calcination Temperature—The term "calcination temperature" refers to the maximum temperature utilized as an intermediate step in the catalyst synthesis procedure intended to remove the hydration sphere from lanthanum ions and allow solid-state exchange between lanthanum and sodium cations in the sodalite and supercages Regeneration Temperature—The solid acid catalyst may be regenerated under flowing hydrogen gas at elevated temperatures in order to hydrocrack heavier hydrocarbons and remove them from the zeolitic structure. The maximum temperature used in this step is referred to as the "regeneration temperature."

Conversion—The term "conversion of a reactant" refers to the reactant mole or mass change between a material flowing into a reactor and a material flowing out of the reactor divided by the moles or mass of reactant in the material flowing into the reactor. For example, if 100 grams of olefin are fed to a reactor and 10 grams of olefin exit the reactor, the conversion is [(100-10)/=100]90% conversion of olefin.

A "crystalline zeotype material" means the material can be detected by x-ray diffraction and that it possesses a three dimensional silica framework with open channels into the material. The materials are also called zeolite structures. A description of a large number of zeolite structures can be found in the Zeomics structural compendium through the website http://helios.princeton.edu/zeomics/; although measurements of channel openings in specific catalysts should be determined by conventional techniques. Although typical zeolites are aluminosilicates, aluminum is not necessary in the catalysts used in the present invention that preferably contain less than 1 wt % Al, preferably <0.5 or <0.1 or <0.01 wt % Al; unless otherwise specified, these compositions refer to the catalyst including binder or, in some preferred embodiments refer to the composition within the crystalline phase. The crystalline zeotype catalyst used for converting methane and/or DME to olefins can be referred to as Si/Ti zeotype catalyst indicating Ti in the zeolite Si—O framework.

"RON" stands for Research octane number and is a well-known measure of fuel quality.

Olefins—As used herein, the term "olefin" has its ordinary meaning in the art, and is used to refer to any unsaturated hydrocarbon containing one or more pairs of carbon atoms linked by a double bond. The term light olefins refers to $C_2$-$C_6$ olefins. In this invention, $C_2$-$C_6$ olefins refers to ethylene, propylene, n-butylenes, isobutylene, and the various isomers of pentene and hexene. The phrase "$C_2$-$C_6$ olefins" has the standard meaning encompassing any combination of olefins in the $C_2$ to C6 range, with no minimum requirement for any of the C2 to C6 compounds.

One of ordinary skill in the art will understand how to determine the pore size (e.g., minimum pore size, average of minimum pore sizes) in a catalyst. For example, x-ray diffraction (XRD) can be used to determine atomic coordinates. XRD techniques for the determination of pore size are described, for example, in Pecharsky, V. K. et at, "Fundamentals of Powder Diffraction and Structural Characterization of Materials," Springer Science+Business Media, Inc., New York, 2005. Other techniques that may be useful in determining pore sizes (e.g., zeolite pore sizes) include, for example, helium pycnometry or low-pressure argon adsorption techniques. These and other techniques are described in Magee, J. S. et at, "Fluid Catalytic Cracking: Science and Technology," Elsevier Publishing Company, Jul. 1, 1993, pp. 185-195. Pore sizes of mesoporous catalysts may be determined using, for example, nitrogen adsorption techniques, as described in Gregg, S. J. at al, "Adsorption, Surface Area and Porosity," 2nd Ed., Academic Press Inc., New York, 1982 and Rouquerol, F. et al, "Adsorption by powders and porous materials. Principles, Methodology and Applications," Academic Press Inc., New York, As is conventional, the phrase "having a molecular dimension of 5.1-5.6 Å" (or the like) refers to the largest channel openings within the MFI structure (not the largest cavity sizes) which limit the size of compounds that can escape the interior of the zeolite. This may also be known as the pore limiting diameter. The presence of the MFI structure can be characterized by x-ray diffraction (XRD), $N_2$ adsorption-desorption isotherms. An example is presented by Silvestre-Albero et al., "Desilication of TS-1 zeolite for the oxidation of bulky molecules," Cat. Comm. 44 (2014) 35-39. As is conventionally understood, the phrase "tetrahedral titania" does not require the titania to be exactly tetrahedral, but that it meets the characteristic values for Ti-substituted zeolites such as those mentioned in conjunction with the paper by Silvestre-Albero et al. As is conventionally known, the stated molecular dimensions within the crystalline structure can be determined by known techniques, particularly the conventional gas adsorption/desorption technique such as that described in the paper by Silvestre-Albero et al. The techniques for determining pore structure should converge to the same values; however, if there is a significant discrepancy, the gas adsorption/desorption technique described in the paper by Silvestre-Albero et al. will be determinative.

Selectivity—The term "selectivity" refers to the amount of production of a particular product (or products) as a percent of all products resulting from a reaction. For example, if 100 grams of products are produced in a reaction and 80 grams of octane are found in these products, the selectivity to octane amongst all products is 80/100=80%. Selectivity can be calculated on a mass basis, as in the aforementioned example, or it can be calculated on a molar basis, where the selectivity is calculated by dividing the moles a particular product by the moles of all products. Unless specified otherwise, selectivity is on a mass basis.

Yield—The term "yield" is used herein to refer to the amount of a product flowing out of a reactor divided by the amount of reactant flowing into the reactor, usually expressed as a percentage or fraction. Mass yield is the mass of a particular product divided by the weight of feed used to prepare that product.

When unspecified, "%" refers to mass % which is synonymous with weight %. Ideal gas behavior is assumed so that mole % is the same as volume % in the gas phase.

As is standard patent terminology, the term "comprising" means "including" and does not exclude additional components. Any of the inventive aspects described in conjunction with the term "comprising" also include narrower embodiments in which the term "comprising" is replaced by the narrower terms "consisting essentially of" or "consisting of." As used in this specification, the terms "includes" or "including" should not be read as limiting the invention but, rather, listing exemplary components. As is standard terminology, "systems" include to apparatus and materials (such as reactants and products) and conditions within the apparatus.

The invention is further elucidated in the examples below. In some preferred embodiments, the invention may be further characterized by any selected descriptions from the examples, for example, within ±20% (or within ±10%) of any of the values in any of the examples, tables or figures; however, the scope of the present invention, in its broader aspects, is not intended to be limited by these examples.

Example 1

The starting material was a commercial 13 X molecular sieve from Sigma Aldrich having a SiO2/Al2O3 molar ratio of 2.8 (Si/Al of 1.4) and a sodium content of 15% by weight. This adsorbent is designated as Adsorbent A.

Example 2

The 13X molecular sieve was ion-exchanged by suspending 15 grams of the molecular in 150 mL of 0.2 M Lanthanum nitrate solution and heated to 80° C. while stirring for 2 hours. The lanthanum solution was decanted and replaced with a fresh solution. The ion-exchanges were repeated two more times followed by 2 water washes of 75 mL each. The molecular sieve was then left to dry at room temperature. Following the ion-exchange, the molecular sieve was calcined in a muffle furnace at a temperature of 450° C. for 4 hours. This adsorbent is designated as Adsorbent B.

Example 3

The 13X molecular sieve was ion-exchanged by suspending 15 grams of the molecular sieve in 150 mL of 0.2 M nickel nitrate solution and heated to 80° C. while stirring for 2 hours. The solution was decanted and replaced with a fresh solution. The ion-exchanges were repeated two more times followed by 2 water washes of 75 mL each. The molecular sieve was then left to dry at room temperature. Following the ion-exchange, the molecular sieve was calcined in a muffle furnace at a temperature of 450° C. for 4 hours. This adsorbent is designated as Adsorbent C.

Example 4

The 13X molecular sieve was ion-exchanged by suspending 15 grams of the molecular sieve was suspended in 150 mL of 0.2 M copper nitrate solution and heated to 80° C. while stirring for 2 hours. The nitrate solution was decanted and replaced with a fresh solution. The ion-exchanges were repeated two more times followed by 2 water washes of 75 mL each. The molecular sieve was then left to dry at room temperature. Following the ion-exchange, the molecular sieve was calcined in a muffle furnace at a temperature of 450° C. for 4 hours. This adsorbent is designated as Adsorbent D.

Example 5

The 13X molecular sieve was ion-exchanged by suspending 15 grams of the molecular sieve was suspended in 150 mL of 0.2 M barium nitrate solution and heated to 80° C. while stirring for 2 hours. The nitrate solution was decanted and replaced with a fresh solution. The ion-exchanges were repeated two more times followed by 2 water washes of 75 mL each. The molecular sieve was then left to dry at room temperature. Following the ion-exchange, the molecular sieve was calcined in a muffle furnace at a temperature of 450° C. for 4 hours.

The ion-exchanged molecular sieve was suspended in a 0.5 M ammonium nitrate solution and heated to 80° C. with stirring for 2 hours. The ammonium solution was decanted and replaced with fresh solution. This ion exchange was performed 3 times followed by 2 water washes of 75 mL each. The ion-exchanged molecular sieve was then dried and calcined at 450° C. for 4 hours. This adsorbent is designated as Adsorbent E.

Example 6

The 13X molecular sieve was ion-exchanged by suspending 15 grams of the molecular sieve was suspended in 150 mL of 0.2 M calcium nitrate solution and heated to 80° C. while stirring for 2 hours. The nitrate solution was decanted and replaced with a fresh solution. The ion-exchanges were repeated two more times followed by 2 water washes of 75 mL each. The molecular sieve was then left to dry at room temperature. Following the ion-exchange, the molecular sieve was calcined in a muffle furnace at a temperature of 450° C. for 4 hours.

The ion-exchanged molecular sieve was suspended in a 0.5 M ammonium nitrate solution and heated to 80° C. with stirring for 2 hours. The ammonium solution was decanted and replaced with fresh solution. This ion exchange was performed 3 times followed by 2 water washes of 75 mL each. The ion-exchanged molecular sieve was then dried and calcined at 450° C. for 4 hours. This adsorbent is designated as Adsorbent F.

Example 7

Alkylation activity experiments were performed using an isothermal packed bed reactor setup shown in FIG. 1 such that the $d_T/d_p > 10$ and the $L/d_p > 50$. Heating was controlled using an Omega temperature control unit and a ceramic heating element. Feeds were sent through a preheater of ~75 cm length prior to entering the reactor.

ExSact-3000 catalyst (15 gm) and adsorbent of interest (10 gm) were first loaded into a reactor and activated by flowing 1 LPM of nitrogen at 350° C. for 4 hours and then cooled to the reaction temperature of 45° C. The reactor was then pressurized with iso-butane to 300 psig. The reaction feed mixture of excess iso-butane and 1-butene was fed to the reactor at a WHSV of 1/hr. The recycle ratio was maintained at 40 vol/vol. Product samples were withdrawn hourly and analyzed using a gas chromatograph equipped with a Petrocol DH 100 m column. The effect of adsorbents on the performance of ExSact 3000 catalyst for alkylation of 1-butene with isobutane is shown in Table 1.

TABLE 1

Performance of adsorbents using 13X molecular sieve

| Adsorbent # | Starting Material | $1^{st}$ Exchange | $2^{nd}$ Exchange | Catalyst Lifetime |
|---|---|---|---|---|
| None | | | | Base |
| A | 13 X | none | none | 0 |
| B | 13 X | $La^{+3}$ | none | 1.23 Base |
| C | 13 X | $Ni^{+2}$ | none | Base |
| D | 13 X | $Cu^{+2}$ | none | Base |
| E | 13 X | $Ba^{+2}$ | $NH^{4+}$ | 0.8 Base |
| F | 13 X | $Ca^{+2}$ | $NH^{4+}$ | 0.8 Base |

Table 1 shows the benefits of using a RE-exchanged molecular sieve as an adsorbent Example 8

The 13X molecular sieve was ion-exchanged by suspending 15 grams of the molecular sieve was suspended in 150 mL of 0.8 M lanthanum nitrate solution and heated to 80° C. while stirring for 2 hours. The nitrate solution was decanted and replaced with a fresh solution. The ion-exchanges were repeated two more times followed by 2 water washes of 75 mL each. The molecular sieve was then left to dry at room temperature. Following the ion-exchange, the molecular sieve was calcined in a muffle furnace at a temperature of 600° C. for 4 hours.

The ion-exchanged molecular sieve was suspended in a 0.2 M barium nitrate solution and heated to 80° C. with stirring for 2 hours. The nitrate solution was decanted and replaced with fresh solution. This ion exchange was performed 3 times followed by 2 water washes of 75 mL each. The ion-exchanged molecular sieve was then dried and calcined at 450° C. for 4 hours. This adsorbent is designated as Adsorbent G.

Example 9

The 13X molecular sieve was ion-exchanged by suspending 15 grams of the molecular sieve was suspended in 150 mL of 0.8 M lanthanum nitrate solution and heated to 80° C. while stirring for 2 hours. The nitrate solution was decanted and replaced with a fresh solution. The ion-exchanges were repeated two more times followed by 2 water washes of 75 mL each. The molecular sieve was then left to dry at room temperature. Following the ion-exchange, the molecular sieve was calcined in a muffle furnace at a temperature of 600° C. for 4 hours.

The ion-exchanged molecular sieve was suspended in a 0.2 M lithium nitrate solution and heated to 80° C. with stirring for 2 hours. The nitrate solution was decanted and replaced with fresh solution. This ion exchange was performed 3 times followed by 2 water washes of 75 mL each. The ion-exchanged molecular sieve was then dried and calcined at 450° C. for 4 hours. This adsorbent is designated as Adsorbent H.

Example 10

The 13X molecular sieve was ion-exchanged by suspending 15 grams of the molecular sieve was suspended in 150 mL of 0.8 M lanthanum nitrate solution and heated to 80° C. while stirring for 2 hours. The nitrate solution was decanted and replaced with a fresh solution. The ion-exchanges were repeated two more times followed by 2 water washes of 75 mL each. The molecular sieve was then left to dry at room temperature. Following the ion-exchange, the molecular sieve was calcined in a muffle furnace at a temperature of 600° C. for 4 hours.

The ion-exchanged molecular sieve was suspended in a 0.2 M calcium nitrate solution and heated to 80° C. with stirring for 2 hours. The nitrate solution was decanted and replaced with fresh solution. This ion exchange was performed 3 times followed by 2 water washes of 75 mL each. The ion-exchanged molecular sieve was then dried and calcined at 450° C. for 4 hours. This adsorbent is designated as Adsorbent I.

Example 11

The 13X molecular sieve was ion-exchanged by suspending 15 grams of the molecular sieve was suspended in 150 mL of 0.2 M lanthanum nitrate solution and heated to 80° C. while stirring for 2 hours. The nitrate solution was decanted and replaced with a fresh solution. The ion-exchanges were repeated two more times followed by 2 water washes of 75 mL each. The molecular sieve was then left to dry at room temperature. Following the ion-exchange, the molecular sieve was calcined in a muffle furnace at a temperature of 450° C. for 4 hours.

The ion-exchanged molecular sieve was suspended in a 0.8 M aluminum nitrate solution and heated to 80° C. with stirring for 2 hours. The nitrate solution was decanted and replaced with fresh solution. This ion exchange was performed 3 times followed by 2 water washes of 75 mL each. The ion-exchanged molecular sieve was then dried and calcined at 600° C. for 4 hours. This adsorbent is designated as Adsorbent J.

Example 12

The 13X molecular sieve was ion-exchanged by suspending 15 grams of the molecular sieve was suspended in 150 mL of 0.8 M lanthanum nitrate solution and heated to 80° C. while stirring for 2 hours. The nitrate solution was decanted and replaced with a fresh solution. The ion-exchanges were repeated two more times followed by 2 water washes of 75 mL each. The molecular sieve was then left to dry at room temperature. Following the ion-exchange, the molecular sieve was calcined in a muffle furnace at a temperature of 600° C. for 4 hours.

The ion-exchanged molecular sieve was suspended in a 0.2 M phosphoric acid solution and heated to 80° C. with stirring for 2 hours. The acid solution was decanted and replaced with fresh solution. This ion exchange was performed 3 times followed by 2 water washes of 75 mL each. The ion-exchanged molecular sieve was then dried and calcined at 450° C. for 4 hours. This adsorbent is designated as Adsorbent K.

Example 13

The 13X molecular sieve was ion-exchanged by suspending 15 grams of the molecular sieve was suspended in 150 mL of 0.8 M lanthanum nitrate solution and heated to 80° C. while stirring for 2 hours. The nitrate solution was decanted and replaced with a fresh solution. The ion-exchanges were repeated two more times followed by 2 water washes of 75 mL each. The molecular sieve was then left to dry at room temperature. Following the ion-exchange, the molecular sieve was calcined in a muffle furnace at a temperature of 600° C. for 4 hours.

The ion-exchanged molecular sieve was suspended in a 0.2 M lanthanum nitrate solution and heated to 80° C. with stirring for 2 hours. The nitrate solution was decanted and replaced with fresh solution. This ion exchange was performed 3 times followed by 2 water washes of 75 mL each. The ion-exchanged molecular sieve was then dried and calcined at 450° C. for 4 hours. This adsorbent is designated as Adsorbent L.

Example 14

The 13X molecular sieve was ion-exchanged by suspending 15 grams of the molecular sieve was suspended in 150 mL of 0.8 M lanthanum nitrate solution and heated to 80° C. while stirring for 2 hours. The nitrate solution was decanted and replaced with a fresh solution. The ion-exchanges were repeated two more times followed by 2 water washes of 75 mL each. The molecular sieve was then left to dry at room temperature. Following the ion-exchange, the molecular sieve was calcined in a muffle furnace at a temperature of 600° C. for 4 hours.

The ion-exchanged molecular sieve was suspended in a 0.2 M boric acid solution and heated to 80° C. with stirring for 2 hours. The acid solution was decanted and replaced with fresh solution. This ion exchange was performed 3 times followed by 2 water washes of 75 mL each. The ion-exchanged molecular sieve was then dried and calcined at 450° C. for 4 hours. This adsorbent is designated as Adsorbent M.

Example 15

The 13X molecular sieve was ion-exchanged by suspending 15 grams of the molecular sieve was suspended in 150 mL of 0.8 M lanthanum nitrate solution and heated to 80° C. while stirring for 2 hours. The nitrate solution was decanted and replaced with a fresh solution. The ion-exchanges were repeated two more times followed by 2 water washes of 75 mL each. The molecular sieve was then left to dry at room temperature. Following the ion-exchange, the molecular sieve was calcined in a muffle furnace at a temperature of 600° C. for 4 hours.

The ion-exchanged molecular sieve was suspended in a 0.2 M nickel nitrate solution and heated to 80° C. with stirring for 2 hours. The nitrate solution was decanted and replaced with fresh solution. This ion exchange was performed 3 times followed by 2 water washes of 75 mL each. The ion-exchanged molecular sieve was then dried and calcined at 450° C. for 4 hours. This adsorbent is designated as Adsorbent N.

Example 16

The 13X molecular sieve was ion-exchanged by suspending 15 grams of the molecular sieve was suspended in 150 mL of 0.8 M lanthanum nitrate solution and heated to 80° C. while stirring for 2 hours. The nitrate solution was decanted and replaced with a fresh solution. The ion-exchanges were repeated two more times followed by 2 water washes of 75 mL each. The molecular sieve was then left to dry at room temperature. Following the ion-exchange, the molecular sieve was calcined in a muffle furnace at a temperature of 600° C. for 4 hours.

The ion-exchanged molecular sieve was suspended in a 0.2 M copper nitrate solution and heated to 80° C. with stirring for 2 hours. The nitrate solution was decanted and replaced with fresh solution. This ion exchange was performed 3 times followed by 2 water washes of 75 mL each. The ion-exchanged molecular sieve was then dried and calcined at 450° C. for 4 hours. This adsorbent is designated as Adsorbent O.

Example 17

The 13X molecular sieve was ion-exchanged by suspending 15 grams of the molecular sieve was suspended in 150 mL of 0.8 M lanthanum nitrate solution and heated to 80° C. while stirring for 2 hours. The nitrate solution was decanted and replaced with a fresh solution. The ion-exchanges were repeated two more times followed by 2 water washes of 75 mL each. The molecular sieve was then left to dry at room temperature. Following the ion-exchange, the molecular sieve was calcined in a muffle furnace at a temperature of 600° C. for 4 hours.

The ion-exchanged molecular sieve was suspended in a 0.2 M cobalt nitrate solution and heated to 80° C. with stirring for 2 hours. The nitrate solution was decanted and replaced with fresh solution. This ion exchange was performed 3 times followed by 2 water washes of 75 mL each. The ion-exchanged molecular sieve was then dried and calcined at 450° C. for 4 hours. This adsorbent is designated as Adsorbent P.

Example 18

Alkylation activity experiments were performed as described in Example 7. Results are summarized in table 2.

TABLE 2

Performance of adsorbents using RE-exchanged 13X molecular sieves

| Adsorbent # | Starting Material | $1^{st}$ Exchange | $2^{nd}$ Exchange | Catalyst Lifetime |
|---|---|---|---|---|
| G | 13 X | $La^{+3}$ | $Ba^+$ | 0 |
| H | 13 X | $La^{+3}$ | $Li^+$ | Base |
| I | 13 X | $La^{+3}$ | $Ca^{+2}$ | Base |
| J | 13 X | $La^{+3}$ | $Al^{+3}$ | 0.86 Base |
| K | 13 X | $La^{+3}$ | $PO_4^{-}$ | Base |
| L | 13 X | $La^{+3}$ | $La^{+3}$ | 0.76 Base |
| M | 13 X | $La^{+3}$ | $B^+$ | 0.54 Base |
| N | 13 X | $La^{+3}$ | $Ni^{+2}$ | 1.5 Base |
| O | 13 X | $La^{+3}$ | $Cu^{+2}$ | 3 Base |
| P | 13 X | $La^{+3}$ | $Co+2$ | 4 Base |

Table 2 shows benefits of performing a second ion-exchanged with either Cobalt (Group 9), Nickel (Group 10) or Copper (Group 11) when using a RE-exchanged molecular sieve as an adsorbent

Example 19

The starting material was a commercial NaY molecular sieve from Sigma Aldrich having a SiO2/Al2O3 molar ratio of 5.2 and a sodium content of 13% by weight. This adsorbent is designated as Adsorbent Q.

Example 19

The NaY molecular sieve was ion-exchanged by suspending 15 grams of the molecular sieve was suspended in 150 mL of 0.2 M lanthanum nitrate solution and heated to 80° C. while stirring for 2 hours. The nitrate solution was decanted and replaced with a fresh solution. The ion-exchanges were repeated two more times followed by 2 water washes of 75 mL each. The molecular sieve was then left to dry at room temperature. Following the ion-exchange, the molecular sieve was calcined in a muffle furnace at a temperature of 450° C. for 4 hours.

The RE-exchanged NaY molecular sieve was suspended in a 0.2 M copper nitrate solution and heated to 80° C. with stirring for 2 hours. The nitrate solution was decanted and replaced with fresh solution. This ion exchange was performed 3 times followed by 2 water washes of 75 mL each. The ion-exchanged molecular sieve was then dried and calcined at 450° C. for 4 hours. This adsorbent is designated as Adsorbent R.

Example 20

The adsorbent was prepared by adding copper nitrate solution on to the high surface area g-alumina support via incipient wetness technique. The adsorbent was then left to dry at room temperature. Following the impregnation, the adsorbent was dried and calcined in a muffle furnace at a temperature of 450° C. for 4 hours. This adsorbent is designated as Adsorbent S.

Example 21

Alkylation activity experiments were performed as described in Example 7. Results are summarized in table 3.

TABLE 3

Performance of adsorbents using NaY molecular sieves and g-alumina as starting material

| Adsorbent # | Starting Material | 1$^{st}$ Exchange | 2$^{nd}$ Exchange | Catalyst Lifetime |
|---|---|---|---|---|
| Q | NaY | none | none | 0 |
| R | NaY | La$^{+3}$ | Cu$^{+2}$ | Base |
| S | Al$_2$O$_3$ | 8 wt % Cu | none | Base |

Table 3 shows neither RE-exchanged Y zeolite with Copper nor copper impregnated on g-alumina provides benefits as an adsorbent for paraffin alkylation.

LITERATURE CITED

1. Herden, H. et al. "Liquid phase adsorption studies of octene-1 and octane on X-zeolites." Journal of Colloid and Interface Science 102 (1984): 227-231.
2. R. W. Rousseau, Handbook of Separation Process Technology, John Wiley & Sons, New York, 1987, p. 1024.
3. Cotton, F. A.; Wilkinson, G. Advanced Inorganic Chemistry, 2nd ed.; Interscience: New York, 1966; Chapters 25 and 28.
4. Quinn, H. W. In Progress in Separation and Purification; Perry, E. S. Ed.; Interscience: New York, 1971; Vol. 4.
5. Ho, W. S.; Doyle, G.; Savage, D. W.; Pruett, R. L. Ind. Eng. Chem. Res. 1998, 27, 334.
6. Blytas, G. C. In Separation and Purification Technology, Li, N. N., Cabo, J. M., Eds.; Marcel Dekker: New York, 1992. (10) Safarik, D. J.; Eldridge, R. B. Ind. Eng. Chem. Res. 1998, 37, 2571.
7. Liu, Y.; Li, R.; Sun, H.; Hu, R. Effects of catalyst composition on the ionic liquid catalyzed isobutane/2-butene alkylation. J. Mol. Catal. A: Chem. 2015, 398, 133-139.
8. Padin, J.; Yang, R. T.; Munson, C. L. Ind. Eng. Chem. Res. 1999, 38, 3614.
9. Takahashi, A.; Yang, R. T.; Munson, C. L.; Chinn, D. Ind. Eng. Chem. Res. 2001, 40, 3979.
10. Takahashi, A.; Yang, R. T.; Munson, C. L.; Chinn, D. Cu(I)—Y Zeolite as a Superior Adsorbent for Diene/Olefin Separation. Langmuir 2001, 17, 8405-8413.
11. Jin, M.; Kim, S. S.; Kim, Y. D.; Park, J.-N.; Kim, J. H.; Ko, C. H.; Kim, J.-N.; Kim, J. M. Redox-buffer effect of Fe2+ ions on the selective olefin/paraffin separation and hydrogen tolerance of a Cu+—based mesoporous adsorbent. J. Mater. Chem. A 2013, 1, 6653-6657.
12. Yang, R. T.; Kikkinides, E. S. AIChE J. 1995, 41, 509.
13. Wu, Z.; Han, S. S.; Cho, S. H.; Kim, J. N.; Chue, K. T.; Yang, R. T. Ind. Eng. Chem. Res. 1997, 36, 2749.
14. Cheng, L. S.; Yang, R. T. Adsorption 1995, 1, 61.
15. Padin, J.; Yang, R. T. Ind. Eng. Chem. Res. 1997, 36, 4224.
16. Rege, S. U.; Padin, J.; Yang, R. T. AIChE J. 1998, 44, 799.
17. Padin, J.; Yang, R. T. Chem. Eng. Sci. 2000, 55, 2607.
18. Denayer, Joeri & Huybrechts, Bart & Depla, Anouschka & Hermans, Yves & Gemoets, Frederik & Buren, Frederik & Kirschhock, Christine & Baron, Gino & Pierre, Jacobs. (2007). Removal of cyclopentadiene from 1-octene by transition metal containing zeolites. Part 1: Screening of the adsorption properties. Microporous and Mesoporous Materials. 103. 1-10.
19. Denayer, Joeri & Depla, Anouschka & Vermandel, Walter & Gemoets, Frederik & Buren, Frederik & Martens, Johan & Kirschhock, Christine & Baron, Gino & Pierre, Jacobs. (2007). Removal of cyclopentadiene from 1-octene by transition metal containing zeolites—Part 2: Stabilization of CoCaX zeolite by its cation distribution. Microporous and Mesoporous Materials. 103. 11-19.
20. Jayaraman, A.; Yang, R. T.; Munson, C. L.; Chinn, D., "Deactivation of L-Complexation Adsorbents by Hydrogen and Rejuvenation by Oxidation." Ind. Eng. Chem. Res., 2001, 40, 4370.

What is claimed is:

1. A method of alkylating isobutane, comprising:
   passing a feed mixture consisting of excess isobutane and C2 to C5 olefins into a reaction chamber;
   wherein the reaction chamber comprises a catalyst system comprising:
      a crystalline zeolite catalyst comprising sodalite cages and supercages, a Si/Al molar ratio of 20 or less, less than 0.5 weight percent alkali metals; and up to 5 wt % of Pt, Pd and or Ni, and acid-site density (including both Lewis and Brønsted acid sites) of at least 100 µmole/gm; and
      a RE-modified molecular sieve adsorbent (Re-MSA) comprising sodalite cages and supercages, a Si/Al molar ratio of 20 or less, less than 1 wt % of alkali metals, RE (rare earth elements) in the range of 10 to 30 wt % and transition metals selected from groups 9-11 in the range from 2 wt % to 10 wt; and acid-site density of no more than 30 µmole/gm.

2. The method of claim 1 wherein, at steady state, at least 90% of the C2-C5 olefins are converted to products comprising C8 isomers, and wherein the Research Octane Number (RON) of the products remains above 90; and conducting the process for a catalyst age of 2.5 or greater over the same catalyst system without regeneration; and wherein steady state means that the selectivity to $C_8$ isomers changes by 10% or less over the entire period that the catalyst age is determined.

3. The method of claim 1 wherein the crystalline zeolite catalyst comprises rare earth elements in the range of 10 to 35 wt %; and
   wherein the Re-MSA comprises a micro-pore diameter of at least 8 Angstroms, or in the range of 8 to 12 Å.

4. The method of claim 1 wherein the concentration of C2 to C5 olefins in the feed is between 1 wt % and 30 wt %.

5. The method of claim 1 wherein at an entrance of a catalyst bed comprising the catalyst system, the ratio of the concentration of iso-butane to the concentration of C2-C5 olefins is between 100-1000 mol/mol.

6. The method of claim 1 wherein crystalline zeolite the catalyst and Re-MSA are regenerated in a flowing gas stream that is essentially hydrogen at a temperature of at least 250° C.; and wherein the crystalline zeolite catalyst comprises 0.1 wt % to 5 wt %, or 0.5 to 4 wt %, or 1.0 to 3.0 wt %, of an element selected from the group consisting of Pt, Pd, Ni, and combinations thereof.

7. The method of claim 1 wherein the reaction chamber comprises a packed crystalline zeolite catalyst bed followed by a Re-MSA bed.

8. The method of claim 1 wherein the reaction chamber comprises alternating beds of crystalline zeolite catalyst and Re-MSA comprising at least 2 crystalline zeolite catalyst beds and 2 Re-MSA beds.

9. The method of claim 1 wherein the reaction chamber comprises a packed bed consisting of a mixture of crystalline zeolite catalyst and Re-MSA.

10. The method of claim 1 conducted at a pressure of 250 to 400 psig.

11. The method of claim 1 wherein the olefin space velocity is between 0.05/hr to 0.5/hr.

12. The method of claim 1 wherein the crystalline zeolite catalyst and Re-MSA are regenerated with a flow of gas which is at least 50 volume % hydrogen.

13. The method of claim 1 wherein the catalyst and Re-MSA is regenerated in flowing hydrogen at a temperature of at least 250° C. and a GHSV of at least 500 $hr^{-1}$.

14. The method of claim 1 wherein the method is run continuously for a catalyst age of 2-3.5 without regenerating the crystalline zeolite catalyst or Re-MSA.

15. The method of claim 1 wherein the reaction chamber comprises a packed Re-MSA bed followed by a crystalline zeolite catalyst bed.

16. The method of claim 1 wherein a ratio of the Re-MSA weight to crystalline zeolite catalyst weight in the reaction chamber is between 0.1 to 10 wt/wt.

17. The method of claim 1 wherein the reaction chamber comprises a packed bed of particles, comprising crystalline zeolite catalyst and Re-MSA wherein at least 95 wt % of the particles have particle diameters of at least 0.1 mm.

18. The method of claim 1 conducted at a temperature between 45 and 90° C.

19. The method of claim 1 wherein the $C_2$ to $C_5$ olefin contains less than 100 ppm water.

20. The method of claim 1 comprising conducting the process for a catalyst age of 2.5 or a catalyst age of 3.0.

* * * * *